United States Patent
Picha et al.

(10) Patent No.: US 8,960,231 B2
(45) Date of Patent: Feb. 24, 2015

(54) MULTI-MODE INJECTION VALVE

(76) Inventors: Neil Robert Picha, Petaluma, CA (US); Bruce D. Black, Napa, CA (US)

( * ) Notice: Subject to any disclaimer, the term of this patent is extended or adjusted under 35 U.S.C. 154(b) by 114 days.

(21) Appl. No.: 13/587,659

(22) Filed: Aug. 16, 2012

(65) Prior Publication Data
US 2013/0068977 A1  Mar. 21, 2013

Related U.S. Application Data (60) Provisional application No. 61/537,487, filed on Sep. 21, 2011.

(51) Int. Cl.
*F16K 11/074* (2006.01)
*G01N 30/20* (2006.01)

(52) U.S. Cl.
CPC .............. *G01N 30/20* (2013.01); *F16K 11/074* (2013.01); *G01N 2030/202* (2013.01)
USPC ...................... 137/625.46; 73/61.55; 73/61.56

(58) Field of Classification Search
CPC .................................................. F16K 11/074
USPC ........ 137/625.11, 625.46; 73/863.72, 863.73, 73/61.56, 61.55
See application file for complete search history.

(56) References Cited

U.S. PATENT DOCUMENTS

| | | | |
|---|---|---|---|
| 3,040,777 A * | 6/1962 | Carson et al. ............. | 137/625.15 |
| 3,223,123 A * | 12/1965 | Young ...................... | 137/625.46 |
| 3,477,207 A | 11/1969 | Auger | |
| 3,744,219 A | 7/1973 | Tindle | |
| 3,868,970 A * | 3/1975 | Ayers et al. .............. | 137/625.46 |
| 4,577,515 A | 3/1986 | Someya | |
| 4,625,569 A | 12/1986 | Toei | |
| 5,010,921 A | 4/1991 | Nohl | |
| 5,465,748 A | 11/1995 | Bowers | |
| 5,803,117 A | 9/1998 | Olsen | |
| 6,672,336 B2 | 1/2004 | Nichols | |
| 6,874,354 B2 | 4/2005 | Cueni | |
| 6,910,503 B2 | 6/2005 | Schick | |
| 6,997,213 B1 | 2/2006 | Towler | |
| 7,213,615 B2 | 5/2007 | Cueni | |
| 7,503,203 B2 | 3/2009 | Gamache | |
| 7,574,901 B2 | 8/2009 | Iwata | |
| 7,819,948 B2 | 10/2010 | Wagner | |
| 8,186,382 B2 * | 5/2012 | Wilen ...................... | 137/625.46 |
| 2009/0145205 A1 | 6/2009 | Hochgraeber | |
| 2010/0032604 A1 | 2/2010 | Wilen | |
| 2010/0058841 A1 | 3/2010 | Wilden | |
| 2010/0127200 A1 * | 5/2010 | Kallback et al. .............. | 251/304 |
| 2011/0024657 A1 | 2/2011 | Tower | |
| 2011/0272855 A1 | 11/2011 | Luongo | |

* cited by examiner

*Primary Examiner* — Stephen M Hepperle
*Assistant Examiner* — R. K. Arundale
(74) *Attorney, Agent, or Firm* — Jerry Haynes Law (57) ABSTRACT

A multi-mode injection valve includes a stator having an outer stator face and an inner stator face; a plurality of fluid ports in the outer stator face; a plurality of fluid orifices in the inner stator face, the fluid orifices disposed in fluid communication with the fluid ports, respectively; a rotor having a rotor surface engaging the inner stator face of the stator; a plurality of rotor grooves in the rotor surface of the rotor, each of the rotor grooves adapted for fluid communication with a pair of the fluid orifices depending upon a rotational or angular position of the rotor with respect to the stator; and an actuator unit engaging the rotor, the actuator unit adapted to rotate the rotor relative to the stator.

17 Claims, 12 Drawing Sheets

MULTI-MODE INJECTION VALVE

CROSS-REFERENCE TO RELATED APPLICATIONS

This application claims the benefit of U.S. Provisional application No. 61/537,487, filed Sep. 21, 2011 and entitled MULTI-MODE INJECTION VALVE, which provisional application is incorporated by reference herein in its entirety.

FIELD OF THE INVENTION

Illustrative embodiments of the present disclosure relate to rotary valves used to introduce a sample into an analysis or purification system as commonly performed in liquid chromatography systems.

BACKGROUND OF THE INVENTION

Analytical instrumentation used to determine chemical composition of samples commonly utilizes injection, switching and selector valves to perform routine fluid switching and injection of samples into pressurized fluid streams. These valves direct the movement or flow of fluid into and out of a number of components. Rotary shear valves are commonly used to direct fluid flow in such applications.

Figure 1:
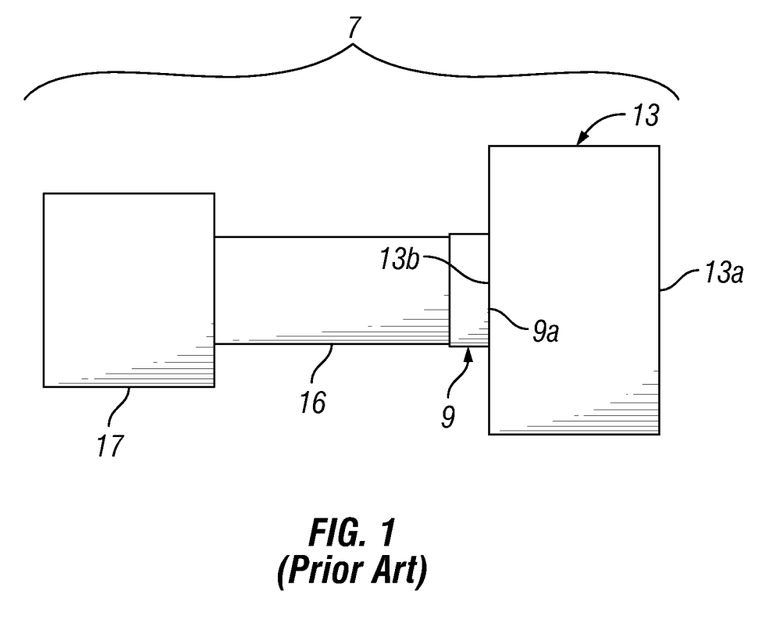
FIG. 1 is a side view of a standard or conventional rotary valve.

A common rotary valve 7 having a conventional design is shown in FIG. 1. A stator 13 having an outer stator face 13a and an inner stator face 13b is fixed to an actuator unit 17 by mechanical means. A rotor 9 is installed on a rotary shaft 16 that is rotated to a designated angle by the actuator unit 17. The rotor 9 has a rotor surface 9a disposed against the inner stator face 13b of the stator 13, as shown.

Figure 2:
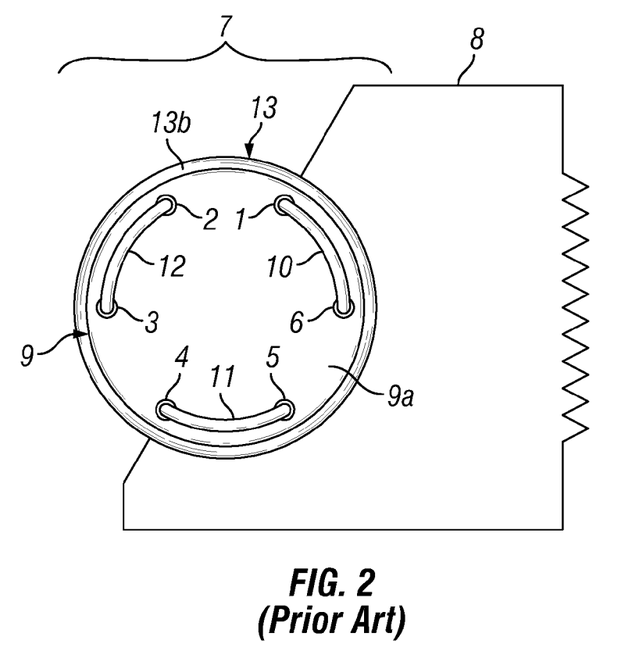
FIG. 2 is an end view of a rotor of the valve illustrated in FIG. 1, more particularly illustrating a first position of the rotor and corresponding alignment of rotor grooves in the rotor with fluid ports in the stator.

Referring to FIG. 2, fluid ports 1-6, respectively, in the outer stator face 13a are disposed in fluid communication with respective fluid orifices (not illustrated) on the inner stator face 13b. The rotor surface 9a of the rotor 9 may be spring-loaded against the inner stator face 13b to provide a constant force which imparts a fluid-tight seal between the rotor surface 9a and the inner stator face 13b. The rotor 9 also allows for rotary motion around the valve's central axis to direct flow of fluid through rotor grooves 10, 11 and 12, respectively, fabricated into the rotor surface 9a. The rotor grooves 10, 11, 12 are disposed in fluid communication with the fluid orifices (not illustrated) on the stator face 13b. The design and complexity of the rotor grooves 10, 11, 12 can allow for many unique connections between the fluid orifices in the stator face 13b to facilitate advantageous fluidic functions.

An example of a common rotary valve is the Cadence Fluidics UBX-1701-0206-0001. This valve is designed for two positions with position one shown in FIG. 2 and position two shown in FIG. 3. The valve has two fluid ports: fluid port 2 allows flow from a liquid supply, such as a chromatographic pump (not illustrated), and a second fluid port 5, which is adapted to receive a fluid sample from a sample syringe (not illustrated). A sample loop 8 may be connected to fluid port 1 and to fluid port 4. Fluid port 6 is an outlet port, or waste port. Fluid port 3 is also an outlet port, and in this example, is connected to a chromatography column.

In FIGS. 1 & 2, the rotor 9 is disc-shaped and has the rotor grooves 10, 11, 12. When the rotor 9 is rotated around its center axis, the rotor grooves 10, 11, 12 align with the fluid orifices in the inner stator face 13b to allow for a change in fluidic pathways. FIG. 2 shows position 1 due to the angular position of the rotor 9 in relation to the stator 13. Two fluidic functions are performed in position 1. The first is connection of the pump to fluid port 2, which is disposed in fluid communication with the chromatography column at fluid port 3 through the rotor groove 12. The second function is connection of the syringe to fluid port 5, which is disposed in fluid communication with a first end of the sample loop 8 through the rotor groove 11 and the fluid port 4. Fluid port 1 is disposed in fluid communication with a second end of the sample loop 8 and also to the rotor groove 10 and the fluid port 6, which is connected to a waste line (not illustrated). This function allows filling of the sample loop 8 by the syringe, with the excess fluid from the syringe going to waste.

Figure 3:
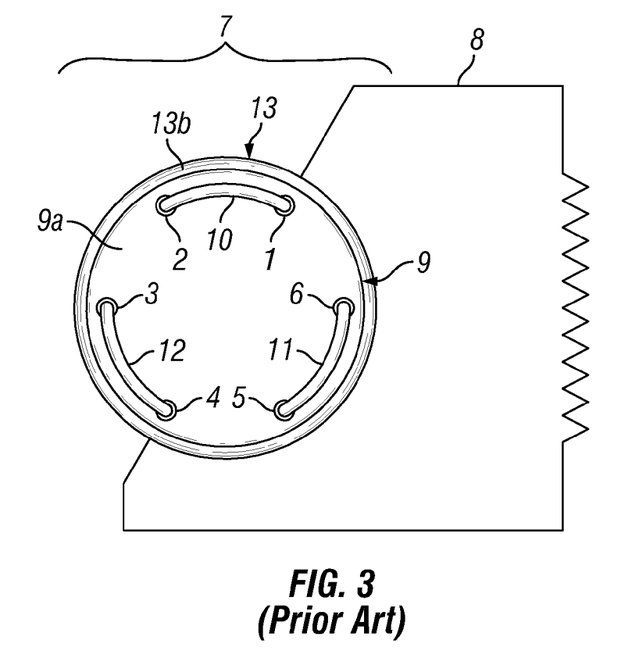
FIG. 3 is an end view of a rotor of the valve illustrated in FIG. 1, more particularly illustrating a second position of the rotor and corresponding alignment of rotor grooves in the rotor with fluid ports in the stator.

FIG. 3 shows the configuration of the rotor grooves 10, 11, 12 in position 2 due to angular rotation of the rotor 9 in relation to the stator 13. This valve position allows two functions. The first function is that the pump connected to the fluid port 2 is now disposed in fluid communication with the chromatography column at the fluid port 3 through the rotor groove 10, the fluid port 1, the sample loop 8, the fluid port 4 and the rotor groove 12. This configuration allows for the sample in the sample loop 8 to be introduced by the pump into the chromatography column. The second function is that the syringe connected to the fluid port 6 is now in fluid communication with the waste line at the fluid port 5 through the rotor groove 11. This function allows excess sample to be pushed out of the syringe, and even refilled with sample.

One feature that needs to be noted is that during load and inject, as shown in FIGS. 2 and 3, the valve 7 rotates to bring the pump in fluid communication with the sample loop 8 and the chromatography column in fluid communication with the opposite end of the sample loop 8. During this injection, it is advantageous to not cross any other orifices, hence communicating only with desired orifices and corresponding fluid ports on the outer stator face 13a. If fluid communication is enabled by the rotor grooves 10, 11, 12 to waste line during the move from load to inject as an example, some of the sample could be lost by moving down these unintended passages as they are passed over on the way to the injection flow path of FIG. 3. Adding multiple modes to the valve 7 can result in less than ideal fluid communications to occur that can result in pressure spikes, pressure drops, contamination and sample loss.

A common rotary valve 7 performs routine sample introduction into a chromatographic system. There is only one mode of sample introduction, that being by the syringe, either manually or automated. In some applications other modes of sample introduction may be desired, and these usually require a different valve to be used. A valve that could perform multiple modes of sample introduction would be advantageous in chromatography applications.

SUMMARY OF THE INVENTION

The disclosure is generally directed to a multi-mode injection valve. An illustrative embodiment of the multi-mode injection valve includes a stator having an outer stator face and an inner stator face; a plurality of fluid ports in the outer stator face; a plurality of fluid orifices in the inner stator face, the fluid orifices disposed in fluid communication with the fluid ports, respectively; a rotor having a rotor surface engaging the inner stator face of the stator; a plurality of rotor grooves in the rotor surface of the rotor, each of the rotor grooves adapted for fluid communication with a pair of the fluid orifices depending upon a rotational or angular position of the rotor with respect to the stator; an actuator unit engaging the rotor, the actuator unit adapted to rotate the rotor relative to the stator; and a plurality of elongated stator face grooves in the inner stator face of the stator and communicating with a plurality of the fluid orifices, respectively.

BRIEF DESCRIPTION OF THE DRAWINGS

The disclosure will now be made, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is non-limiting and is not necessarily to be construed as preferred or advantageous over other implementations. All of the implementations described below are exemplary implementations provided to enable persons skilled in the art to practice the disclosure and are not intended to limit the scope of the appended claims. Moreover, the illustrative embodiments described herein are not exhaustive and embodiments or implementations other than those which are described herein and which fall within the scope of the appended claims are possible. Enhancements can be implemented in order to provide drains to waste in order to relief pressure during rotation from one position to another to eliminate liquid pressure spikes from being introduced to unused ports during rotation of the valve rotor. Furthermore, there is no intention to be bound by any expressed or implied theory presented in the preceding technical field, background, brief summary or the following detailed description. Relative terms such as "upper", "lower", "above", "below", "top", "horizontal" and "vertical" as used herein are intended for descriptive purposes only and are not necessarily intended to be construed in a limiting sense. Also, an intermediary seal, or stator face seal placed between the stator (14) and rotor (18) can be implemented to facilitate connections between ports.

Figure 4:
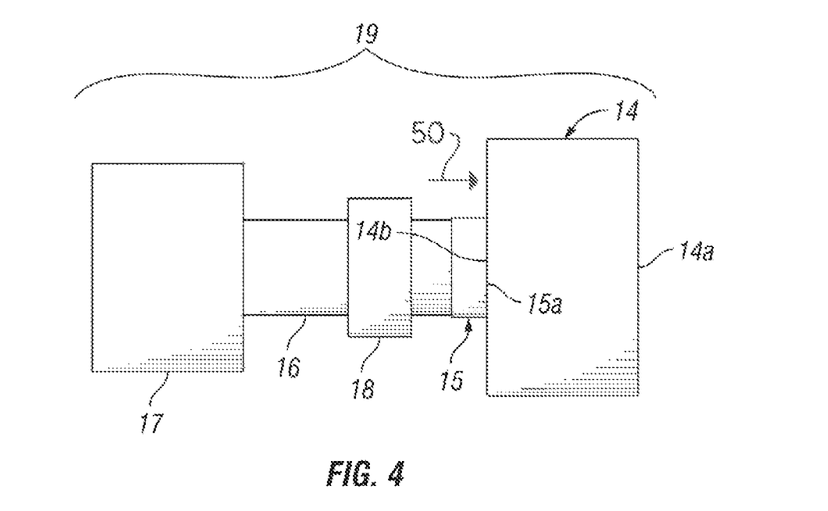
FIG. 4 is a side view of an illustrative embodiment of the multi-mode injection valve according to the disclosure.

Referring to FIGS. 4-14 of the drawings, an illustrative embodiment of a multi-mode injection valve, hereinafter valve, is generally indicated by reference numeral 19. As shown in FIG. 4, the valve 19 includes a stator 14 having an outer stator face 14a and an inner stator face 14b. An actuator unit 17 may mechanically engage the inner stator face 14b of the stator 14 in such a manner that the stator 14 is stationary or non-rotatable relative to the actuator unit 17. A rotary shaft 16 is engaged for rotation by the actuator unit 17. A rotor 18 is installed on the rotary shaft 16. The rotor 18 is rotatable on a rotational axis which coincides with the center axis of the stator 14. The actuator unit 17 is adapted to rotate the rotor 18 as is well known by those skilled in the art. The actuator unit 17 can be operated to rotate the rotor 18 to a designated rotational angle relative to the stator 14 via rotation of the rotary shaft 16.

At least one encoder unit 18 may be provided on the rotary shaft 16 to provide closed-loop electronic feedback which confirms that the rotor 15 is in the correct rotational or angular position relative to the stator 14. Accordingly, the valve 19 has pre-determined positions around the axis of rotation of the rotor 15 that are designated by angular positions which allow selected fluid flow functions to occur, as will be hereinafter described. This selection of fluid flow functions allows for very flexible introduction of fluids into a chromatography column (not illustrated), for example and without limitation, using the valve 19.

As illustrated in FIG. 4, the rotor 15 has a rotor surface 15a disposed against the inner stator face 14b of the stator 14. The rotor surface 15a of the rotor 15 may be spring-loaded 50 against the inner stator face 14b according to the knowledge of those skilled in the art to impart a fluid-tight seal between the rotor surface 15a and the inner stator face 14b. This spring load may be constant and may be adjustable for optimum performance at the working pressure of the system. The inner stator face 14b of the stator 14 may be finished to produce a fluid-tight seal with the rotor surface 15a of the rotor 15.

Figure 5:
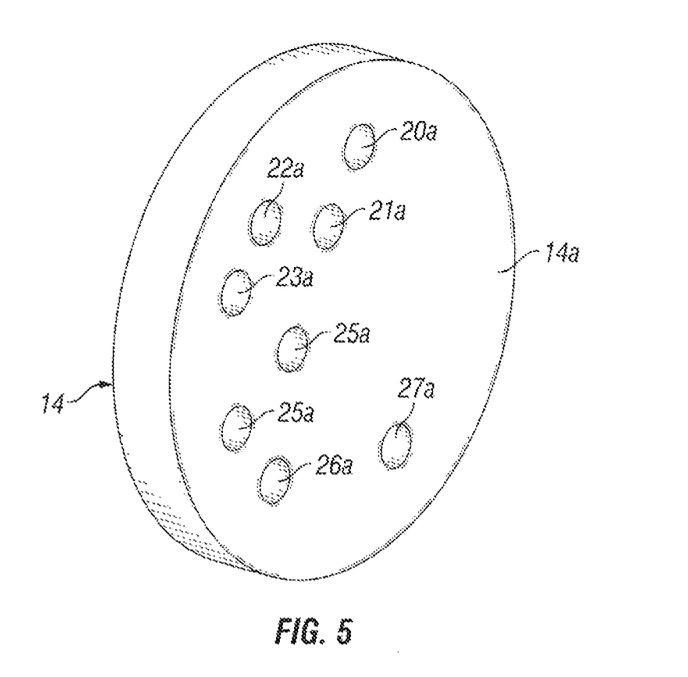
FIG. 5 is a perspective view of an outer stator face of an exemplary stator of the multi-mode injection valve illustrated in FIG. 4, with multiple fluid ports in the outer stator face.
Figure 6:
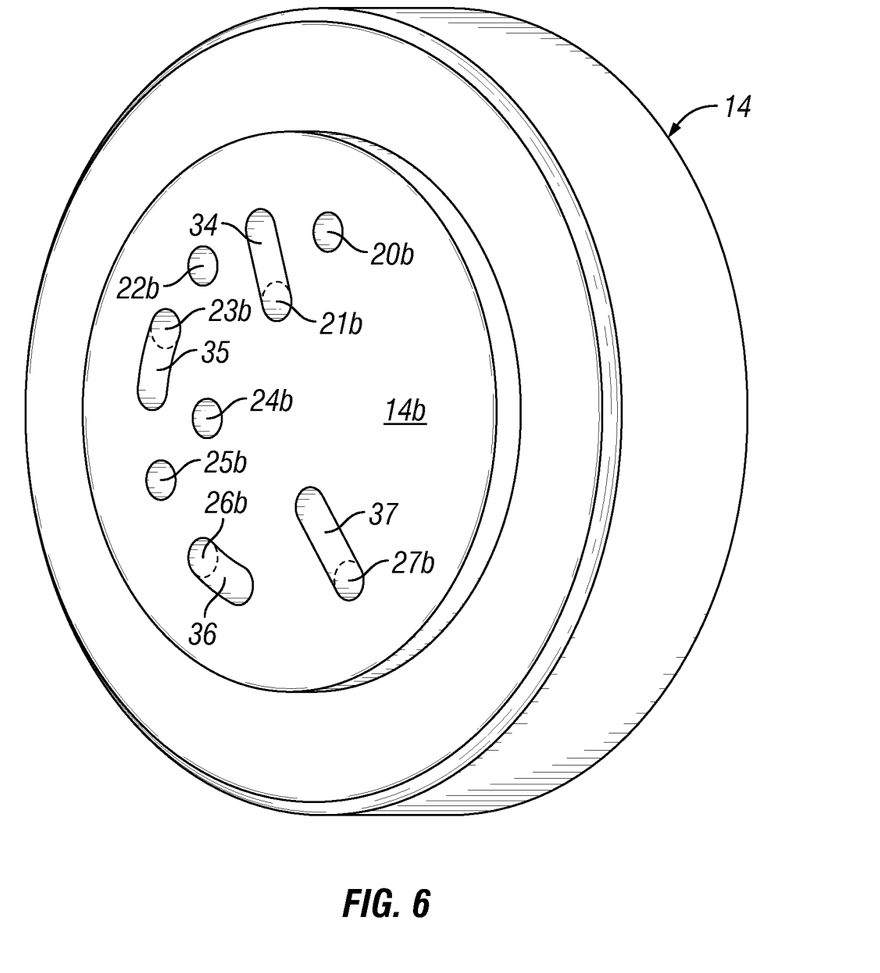
FIG. 6 is a perspective view of an inner stator face of the stator of the multi-mode injection valve, more particularly illustrating an exemplary arrangement of fluid orifices and stator face grooves on the inner stator face.

As illustrated in FIG. 5, fluid ports 20a-27a extend into the outer stator face 14a through the stator 14. The fluid ports 20a-27a are disposed in fluid communication with respective fluid orifices 20b-27b (FIG. 6) in the inner stator face 14b of the stator 14. The fluid ports 20a-27a on the outer stator face 14a are designed and configured to accept industry-standard fittings (not illustrated) such as those available from Optimize Technologies part number 10-21-00291 fitting and 10-21-00296 ferrule for ¼-28 flat bottom ports commonly used in the industry, for example and without limitation. These fittings connect tubing (not illustrated) in a fluid-tight manner to the fluid ports 20a-27a on the outer stator face 14a of the stator 14. The fluid ports 20a-27a may be oriented at multiple angles and orientations relative to the outer stator face 14a to allow proper spacing of the fittings inserted in the fluid ports 20a-27a.

Figure 7:
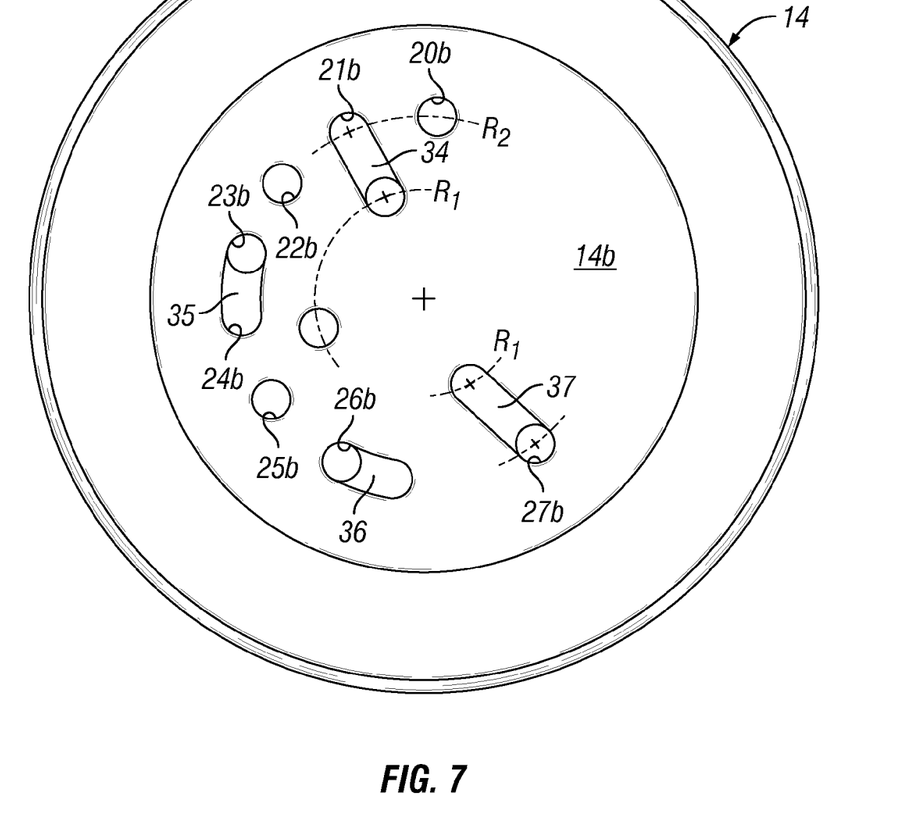
FIG. 7 is a straight-on view of the inner stator face of the stator of the multi-mode injection valve.

As illustrated in FIG. 7, the second fluid orifice 21b and the fifth fluid orifice 24b in the inner stator face 14b may lie along an inner radius R1 which is concentric with the stator 14. All the other fluid orifices 20b, 22b, 23b, 25b, 26b and 27b on the inner stator face 14b may lie along an outer radius R2 which is also concentric with the stator 14 and is greater than the inner radius R1.

As further illustrated in FIG. 7, stator face grooves 34, 35, 36, 37 may be fabricated into the inner stator face 14b of the stator 14. The first stator face groove 34 and the fourth stator face groove 37 may extend in a radial orientation, beginning on the inner radius R1 and extending outwardly to the outer radius R2 to establish fluid communication with the corresponding second fluid orifice 21b and eighth fluid orifice 27b on the stator face 14b. The second stator face groove 35 and the third stator face groove 36 may lie in a circumferential orientation on the outer radius R2.

Figure 8:
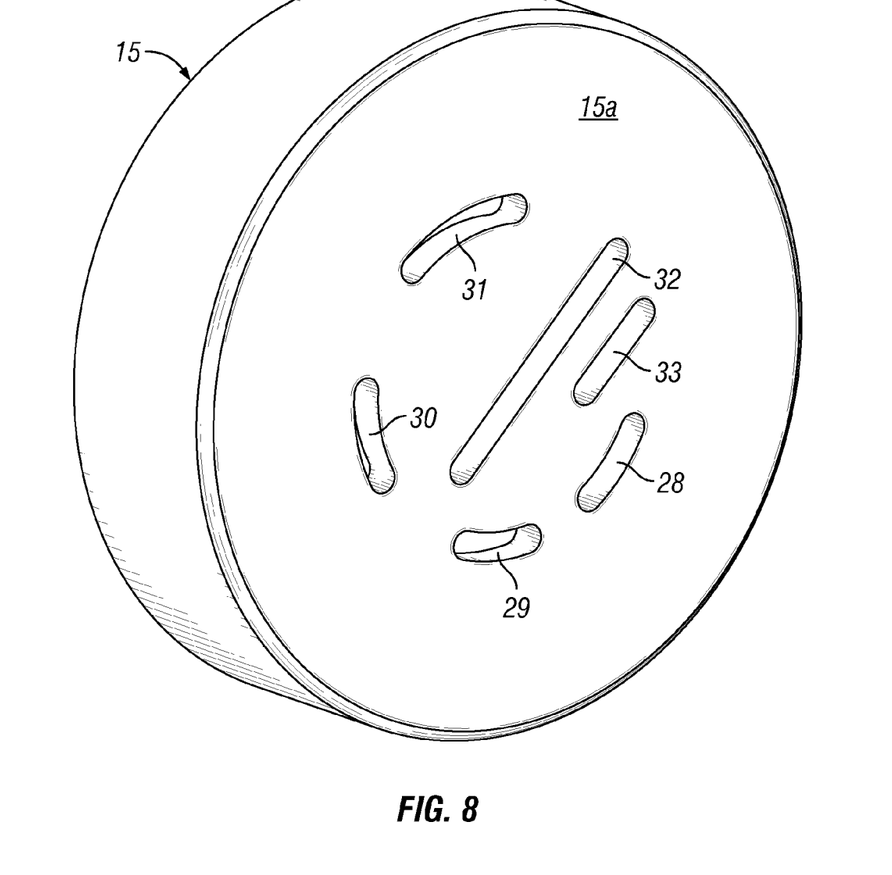
FIG. 8 is a perspective view of a rotor surface of a rotor of the multi-mode injection valve, with an exemplary arrangement of rotor grooves in the rotor surface.
Figure 9:
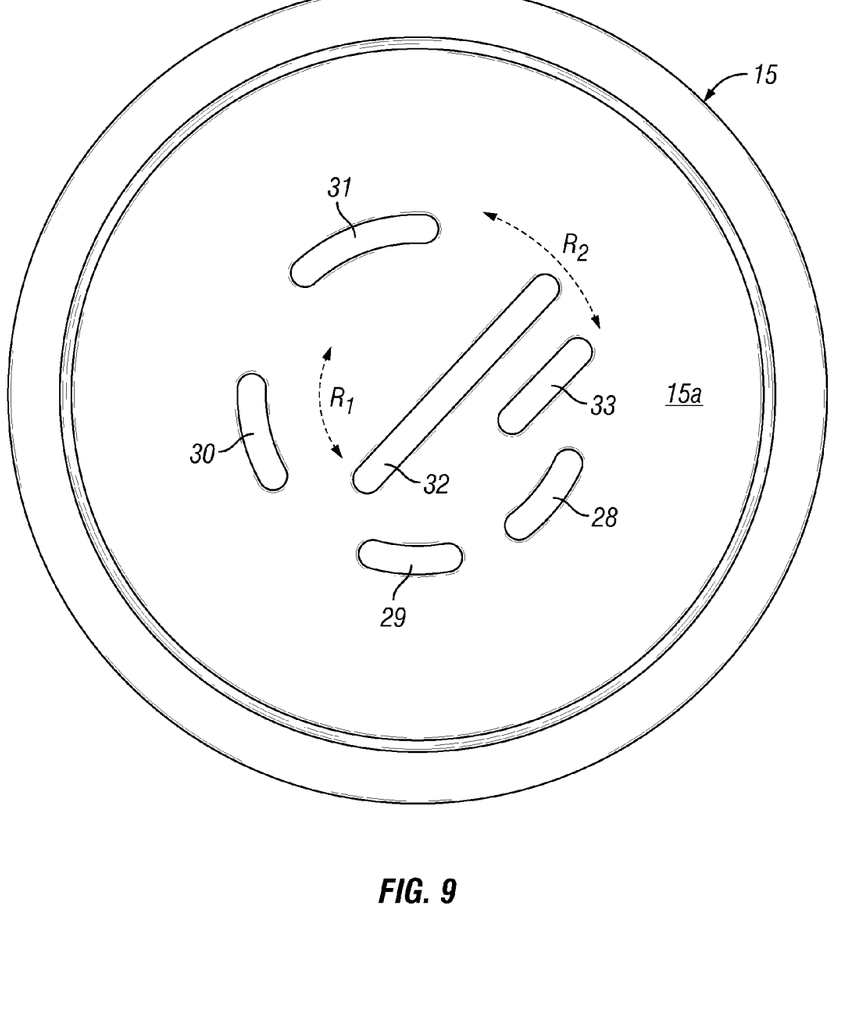
FIG. 9 is a straight-on view of the rotor surface of the rotor.

As illustrated in FIG. 8, multiple rotor grooves 28, 29, 30, 31, 32, 33 may be machined or otherwise provided in the rotor surface 15a of the rotor 15. Depending on the rotational or angular position of the rotor 15 relative to the stator 14, the rotor grooves 28-33 may be disposed in fluid communication with the fluid orifices 20b-27b (FIG. 6) in the inner stator face 14b of the stator 14, either directly (bypassing the stator face grooves 34-37) or indirectly through the stator face grooves 34-37. As illustrated in FIG. 9, the rotor grooves 28, 29, 30 and 31 may lie circumferentially along the outer radius R2. The fifth rotor groove 32 lies with one end on the inner radius R1, and the other end on the outer radius R2. The sixth rotor groove 33 lies on the rotor surface 15a with one end on the outer radius R2 and the other end at a different location on the inner radius R1 than the fifth rotor groove 32. Due to the geometry of this embodiment, and required orifice and groove cross-sectional area, the stator face grooves 34-37 (FIG. 7) in the inner stator face 14b of the stator 14 are adapted to interface in fluid communication with the rotor grooves 28-33 to facilitate multiple functionalities by the rotor grooves 28-33.

Figure 10:
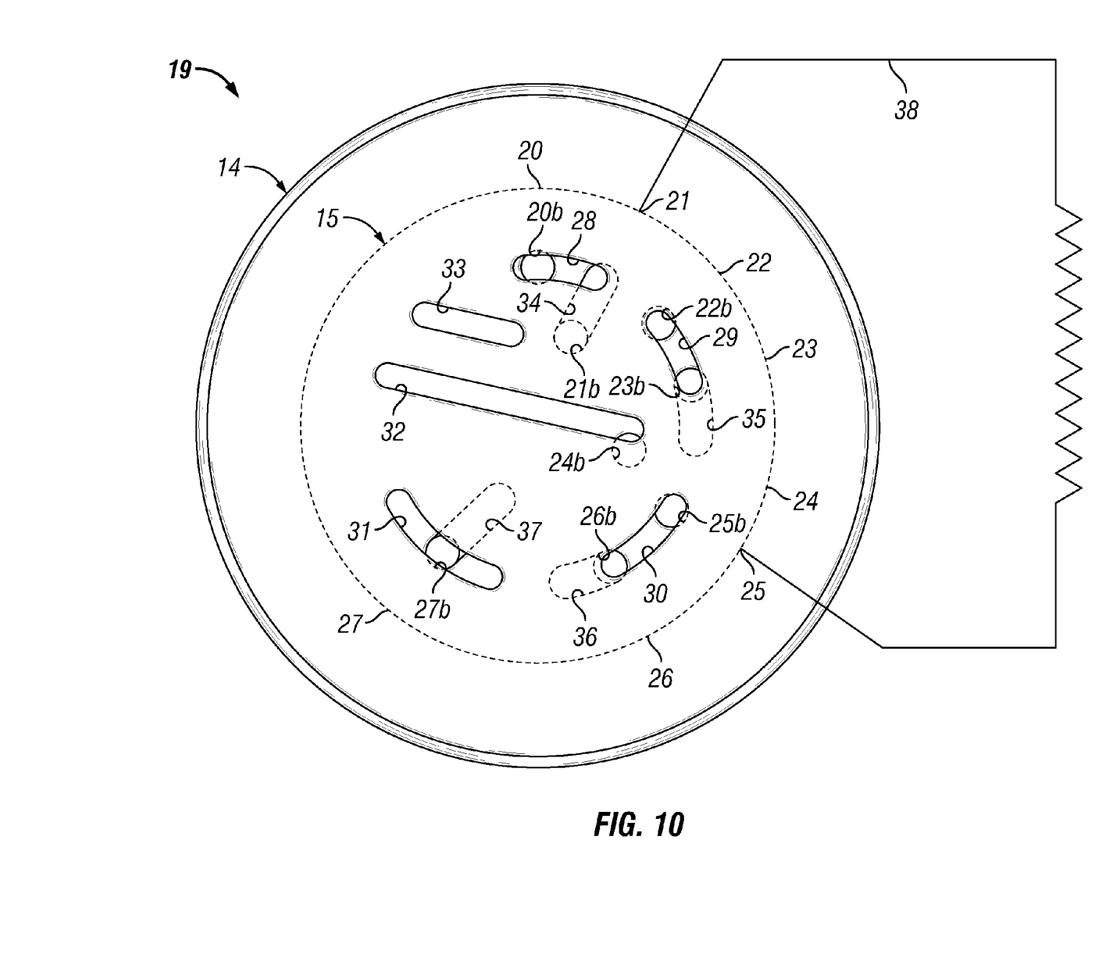
FIG. 10 is a diagram which illustrates rotational or angular positioning of the rotor relative to the stator.

As illustrated in FIG. 10, the valve 19 may have four positions each of which enables two desirable fluidic functions. As illustrated in FIG. 5, the first fluid port 20a on the outer stator face 14a of the stator 14 allows introduction of liquid samples into the valve 19. The second fluid port 21a is a communication port that is connected to a sample loop 38 (FIG. 10) in some embodiments. The sixth fluid port 25a is also a communication port that is connected to the opposite end of the sample loop 38. The third fluid port 22a is an exit port that allows sample and mobile phase, or system fluid to be in fluid communication with a chromatography column (not illustrated). The fourth fluid port 23a is an inlet fluid port that facilitates connection of a system pump (not illustrated) to the valve 19. The fifth fluid port 24a is an exit port to waste. The seventh fluid port 26a is also an exit port to waste. The eighth fluid port 27a is an inlet fluid port that connects to a second pump, or sample introduction pump.

It should be noted that for those skilled in the art, the arrangement of stator face grooves 34-37 in the inner stator face 14b and the rotor surface 15a can be modified to provide the same functionality. For instance, a stator face groove 34-37 in the inner stator face 14b could be moved to the rotor surface 15a to obtain the same functionality, and the fluid orifices 20b-27b on the inner stator face 14b could be rearranged to provide the same functionality. A key characteristic is the fluidic connections made between the fluid orifices 20b-27b on the inner stator face 14b and the rotor grooves 28-33 on the rotor surface 15a at each rotary position, 1 through 4.

Figure 11:
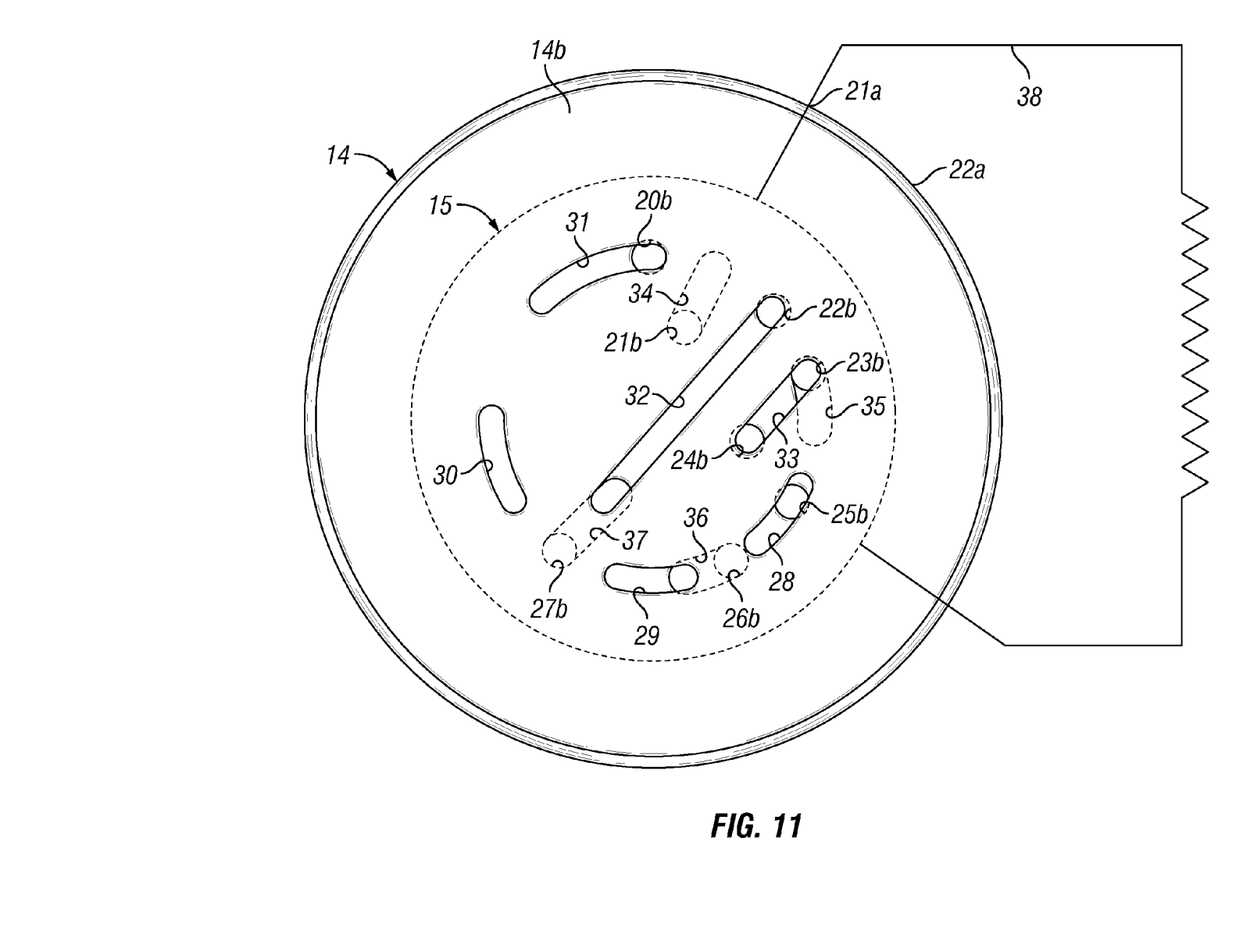
FIG. 11 is a diagram which illustrates a first mode of sample introduction according to a first rotational or angular position of the rotor relative to the stator.

FIG. 11 shows the valve 19 with the rotor 15 in position 1, at an angle a. In this position, two functions are possible and involve rotor grooves 32 and 33, with rotor grooves 28-31 remaining inactive. The first function occurs whereby the fifth rotor groove 32 connects the outlet third fluid orifice 22b with the inlet eighth fluid orifice 27b on the inner stator face 14b indirectly via the fourth stator face groove 37. This connection allows a sample introduction pump (not illustrated) connected to the inlet eighth fluid port 27a (FIG. 5) to communicate directly with the outlet third fluid port 22a, which is connected to the chromatography column (not illustrated). This is considered a first mode of sample introduction. The second function occurs in which the sixth rotor groove 33 connects the inlet fourth fluid orifice 23b to the outlet fifth fluid orifice 24b. In this application, this is intended to connect the sample introduction pump to the inlet fourth fluid port 23a (FIG. 5) directly to a waste outlet at the fifth fluid port 24a, thereby bypassing the chromatography column and the sample loop 38. Those skilled in the art know that there are other ways to make these connections for instance, by connecting directly from the inlet eighth fluid orifice 27b to the outlet third fluid orifice 22b without the intermediary of a stator face groove 34-37 as may be accomplished by, for instance, employing a groove (not illustrated) fabricated into the rotor 15. The geometry requirements are dictated by required pressure, materials, and seal radius. This can be done with narrower grooves, or by having the stator face orifices on the inner stator face 14b be at a larger radius. Depending on required pressure, materials, and geometry, these parameters can be optimized for the geometry required.

Figure 12:
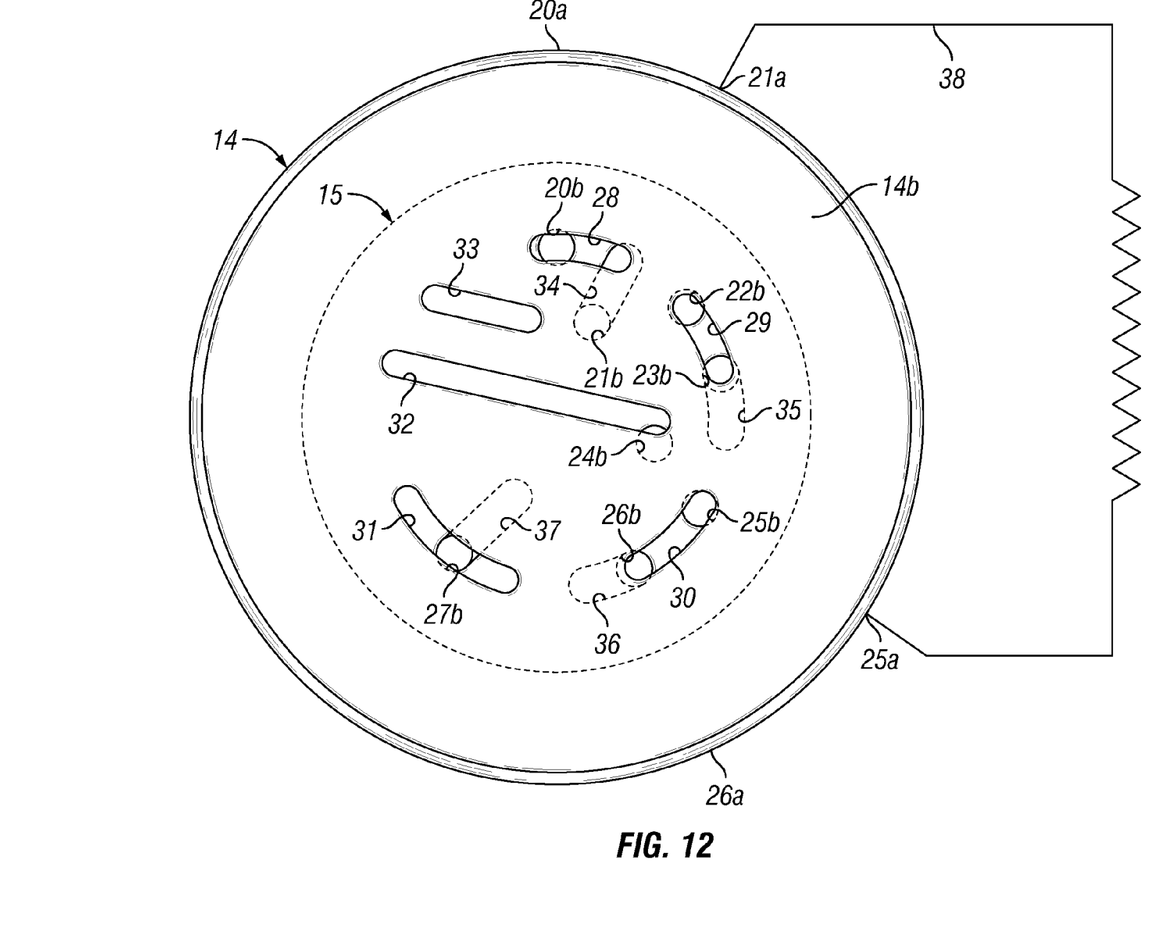
FIG. 12 is a diagram which illustrates a second mode of sample introduction according to a second rotational or angular position of the rotor relative to the stator.

FIG. 12 shows the valve 19 with the rotor 15 in position 2, at an angle θ from position 1 in FIG. 11. In this position, the second rotor groove 29 directly connects the inlet fourth fluid orifice 23b to the outlet third fluid orifice 22b on the inner stator face 14b. Accordingly, the system pump pump (not illustrated) is connected directly to the chromatography column, bypassing the sample loop 38. Pumping of mobile phase into the chromatography column before sample is injected is a common technique. The second connection made in position 2 is where the first rotor groove 28 connects the inlet first fluid orifice 20b to the communication second fluid orifice 21b indirectly via the stator face groove 34, and the third rotor groove 30 directly connects the communication sixth fluid orifice 25b to the outlet seventh fluid orifice 26b. This function allows the injection syringe connected to the inlet first fluid port 20a to inject sample into the sample loop 38, with the excess sample moving out of the valve through the outlet seventh fluid port 26a, and is considered the second mode of sample introduction. The functionality of this position is commonly called the "syringe load position", with the system pump connected directly to the chromatography column for equilibration of the column before injection of the sample.

Figure 13:
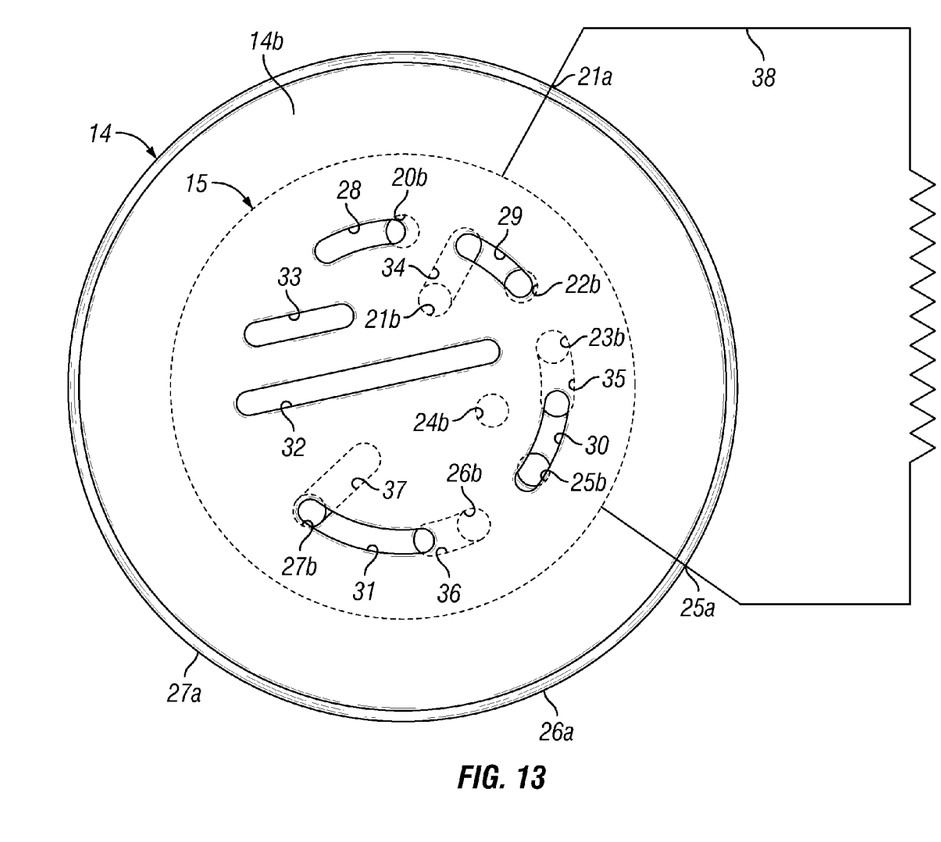
FIG. 13 is a diagram which illustrates a sample injection position according to a third rotational or angular position of the rotor relative to the stator.

FIG. 13 shows the valve 19 with the rotor 15 in position 3, at an angle μ from the rotor position 1 illustrated in FIG. 11. Angle μ would be further in this embodiment from angle a than position 2, or angle β. This position has two functions as shown, and is commonly known as the sample injection position. The third rotor groove 30 on the rotor surface 15a connects the inlet fourth fluid orifice 23b to the communication sixth fluid orifice 25b indirectly via the stator face groove 35, and the second rotor groove 29 connects the communication second fluid orifice 21b with the outlet third fluid orifice 22b indirectly via the stator face groove 34. This position in this embodiment would allow the system pump to move the sample in the sample loop 38 into the chromatography column in the reverse direction that it was loaded in the previous load position in FIG. 12, or position 2. This reverse injection may be desirable in a chromatographic system. The second function that this position allows is where the fourth rotor groove 31 connects the inlet eighth fluid orifice 27b with the outlet seventh fluid orifice 26b indirectly via the third stator face groove 36. In this embodiment, the sample introduction pump connected to the inlet eighth fluid port 27a could be directed to waste out of the outlet seventh fluid port 26a, commonly called the waste port.

Figure 14:
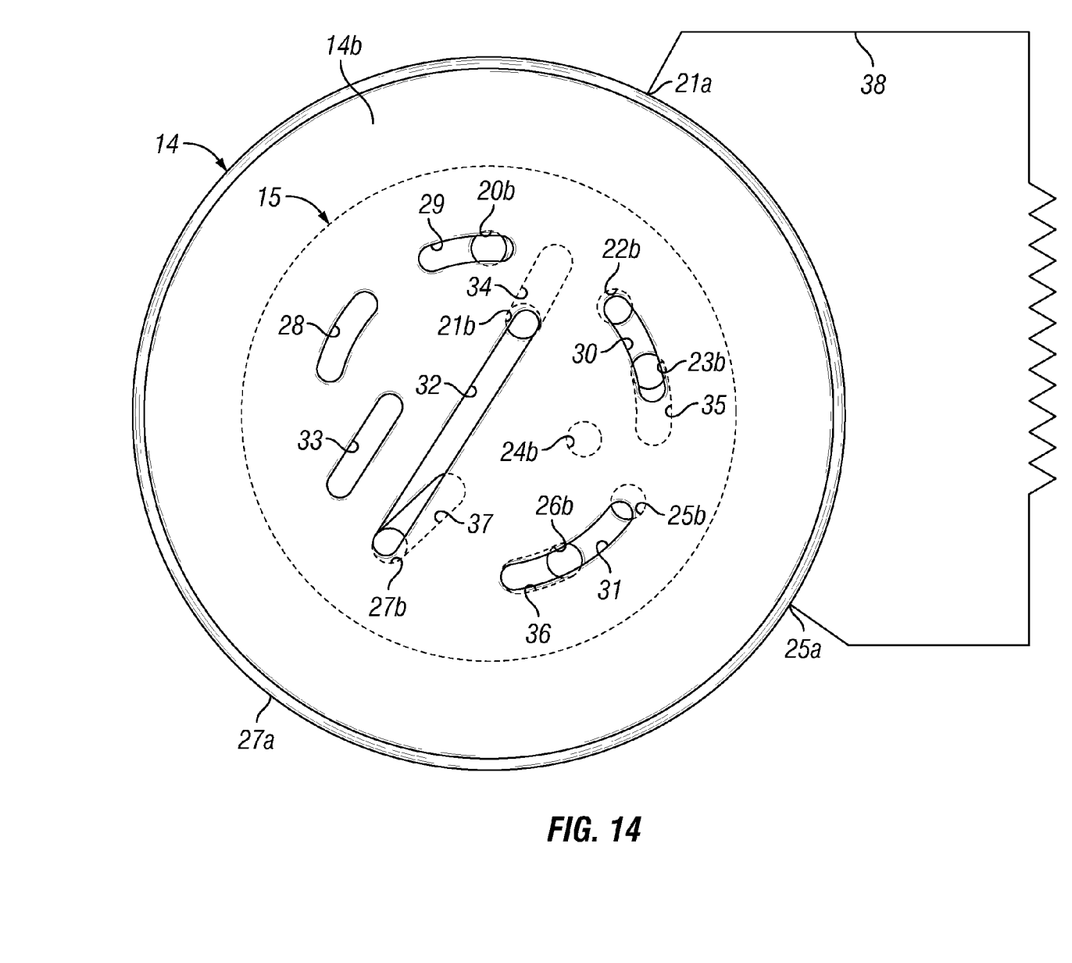
FIG. 14 is a diagram which illustrates a fourth mode of sample introduction according to a fourth rotational or angular position of the rotor relative to the stator.

FIG. 14 shows the valve 19 with the rotor 15 in position 4, at an angle Ω from the first rotor position in FIG. 11. This position has two functions. In the first function, the third rotor groove 30 connects the inlet fourth fluid orifice 23b directly with the outlet third fluid orifice 22b. This function would allow the first pump, or system pump connected to the inlet fourth fluid port 23a to connect to the chromatography column through the outlet third fluid port 22a. In the second function in position 4, the fifth rotor groove 32 connects the inlet eighth fluid orifice 27b directly to the communication second fluid orifice 21b, and the fourth rotor groove 31 connects the communication sixth fluid orifice 25b directly to the waste outlet at the seventh fluid orifice 26b. In this configuration, the sample introduction pump, connected to the eighth fluid port 27a, to come into fluid communication with the communication second fluid orifice 21b, thereby connecting to the sample loop 38. The opposite end of the sample loop 38 is connected through the communication sixth fluid port 25a to the waste outlet at the seventh fluid orifice 26b, and out the valve 19 through the outlet seventh fluid port 26a. Therefore, the sample introduction pump could load sample onto the sample loop 38 with excess sample going to waste. This would be a second means of loading the sample loop 38 using the sample introduction pump connected to the eighth fluid port 27a, and would be a third mode of sample introduction.

While the illustrative embodiments of the disclosure have been described above, it will be recognized and understood that various modifications can be made to the embodiments and the appended claims are intended to cover all such modifications which may fall within the spirit and scope of the disclosure.

What is claimed is:

1. An injection valve, comprising:
a stator having an outer stator face and an inner stator face;
a plurality of fluid ports in the outer stator face;
a plurality of circular fluid orifices in the inner stator face, the fluid orifices disposed in fluid communication with the fluid ports, respectively, a pair of the plurality of fluid orifices lie along an inner radius concentric with the stator;
a rotor having a rotor surface engaging the inner stator face of the stator;
a plurality of rotor grooves in the rotor surface of the rotor, each of the rotor grooves adapted for fluid communication with a pair of the fluid orifices depending upon a rotational or angular position of the rotor with respect to the stator; and
an actuator unit engaging the rotor, the actuator unit adapted to rotate the rotor relative to the stator; and
elongated and discrete first, second, third and fourth stator face grooves in the inner stator face of the stator and communicating with a plurality of the fluid orifices, respectively, the first and fourth stator face grooves extending in a radial orientation beginning on the inner radius and extending outwardly to an outer radius and the second and third stator face grooves lying in a circumferential orientation on the outer radius between the first and fourth stator face grooves.

2. The injection valve of claim 1 wherein the rotor surface of the rotor is spring-loaded against the inner stator face of the stator.

3. The injection valve of claim 1 wherein the plurality of fluid ports comprises eight fluid ports and the plurality of fluid orifices comprises eight fluid orifices.

4. The injection valve of claim 1 further comprising a sample loop establishing fluid communication between a first one of the plurality of fluid ports and a second one of the plurality of fluid ports.

5. The injection valve of claim 1 further comprising a rotary shaft drivingly engaged by the actuator unit and drivingly engaging the rotor for rotation.

6. An injection valve, comprising:
a stator having an outer stator face and an inner stator face;
a plurality of fluid ports in the outer stator face;
a plurality of circular fluid orifices in the inner stator face, the fluid orifices disposed in fluid communication with the fluid ports, respectively, a pair of the plurality of fluid orifices lie along an inner radius concentric with the stator;
elongated and discrete first, second, third and fourth stator face grooves in the inner stator face and disposed in fluid communication with a plurality of the fluid orifices, respectively, the first and fourth stator face grooves extending in a radial orientation and terminating on the inner radius and an outer radius, respectively, concentric with the stator and the second and third stator face grooves extending in a circumferential orientation along the outer radius between the first and fourth stator face grooves;
a rotor having a rotor surface engaging the inner stator face of the stator;
a plurality of rotor grooves in the rotor surface of the rotor, the rotor grooves adapted for direct fluid communication with a pair of the fluid orifices and indirect fluid communication with a pair of the fluid orifices through one of the stator face grooves depending upon a rotational or angular position of the rotor with respect to the stator; and
an actuator unit engaging the rotor, the actuator unit adapted to rotate the rotor relative to the stator.

7. The injection valve of claim 6 wherein the rotor surface of the rotor is spring-loaded against the inner stator face of the stator.

8. The injection valve of claim 6 wherein the plurality of fluid ports comprises eight fluid ports and the plurality of fluid orifices comprises eight fluid orifices.

9. The injection valve of claim 6 further comprising a sample loop establishing fluid communication between a first one of the plurality of fluid ports and a second one of the plurality of fluid ports.

10. The injection valve of claim 6 further comprising a rotary shaft drivingly engaged by the actuator unit and drivingly engaging the rotor for rotation.

11. The injection valve of claim 10 further comprising an encoder unit carried by the rotary shaft.

12. An injection valve, comprising:
a stator having an outer stator face and an inner stator face;
a plurality of fluid ports in the outer stator face;
a plurality of circular fluid orifices in the inner stator face, the fluid orifices disposed in fluid communication with the fluid ports, respectively, a pair of the plurality of fluid orifices lie along an inner radius concentric with the stator;
elongated and discrete first, second, third and fourth stator face grooves in the inner stator face and disposed in fluid communication with a plurality of the fluid orifices, respectively, the first and fourth stator face grooves extending in a radial orientation and terminating on the inner radius and an outer radius, respectively, concentric with the stator and the second and third stator face grooves extending in a circumferential orientation along the outer radius between the first and fourth stator face grooves;

a rotor having a rotor surface engaging the inner stator face of the stator;

a plurality of rotor grooves in the rotor surface of the rotor, the rotor grooves adapted for direct fluid communication with a pair of the fluid orifices and indirect fluid communication with a pair of the fluid orifices through one of the stator face grooves depending upon a rotational or angular position of the rotor with respect to the stator, a first plurality of the rotor grooves extending in a circumferential orientation along the outer radius and a second plurality of the rotor grooves extending in a radial orientation; and an actuator unit engaging the rotor, the actuator unit adapted to rotate the rotor relative to the stator.

13. The injection valve of claim 12 wherein the rotor surface of the rotor is spring-loaded against the inner stator face of the stator.

14. The injection valve of claim 12 wherein the plurality of fluid ports comprises eight fluid ports and the plurality of fluid orifices comprises eight fluid orifices.

15. The injection valve of claim 12 further comprising a sample loop establishing fluid communication between a first one of the plurality of fluid ports and a second one of the plurality of fluid ports.

16. The injection valve of claim 12 further comprising a rotary shaft drivingly engaged by the actuator unit and drivingly engaging the rotor for rotation.

17. The injection valve of claim 16 further comprising an encoder unit carried by the rotary shaft.

* * * * *